United States Patent [19]

Gray et al.

[11] Patent Number: 5,399,859

[45] Date of Patent: Mar. 21, 1995

[54] FLOW METER

[75] Inventors: Gary E. G. Gray; Philip J. Urwin, both of Coventry, United Kingdom

[73] Assignee: Courtaulds Fibres (Holdings) Limited, London, England

[21] Appl. No.: 66,776

[22] Filed: May 24, 1993

[51] Int. Cl.$^6$ .................... G01N 23/16; G01N 22/04
[52] U.S. Cl. .................... 250/308; 250/359.1; 250/360.1; 162/DIG. 6
[58] Field of Search .............. 250/308, 360.1, 359.1; 162/DIG. 6, 263, 123

[56] References Cited

U.S. PATENT DOCUMENTS

| | | | |
|---|---|---|---|
| 3,508,035 | 4/1970 | Worthley | 364/568 |
| 4,453,404 | 6/1984 | Powell et al. | 73/159 |
| 4,845,730 | 7/1989 | Mercer | 378/53 |
| 5,099,118 | 3/1992 | Francis | 250/308 |
| 5,117,686 | 6/1992 | Lorenz | 73/159 |

FOREIGN PATENT DOCUMENTS

| | | |
|---|---|---|
| 0272645 | 6/1988 | European Pat. Off. . |
| 0394128 | 10/1990 | European Pat. Off. . |
| 2910673 | 9/1980 | Germany . |
| 2135352 | 8/1984 | United Kingdom . |

OTHER PUBLICATIONS

Richard A. Reese, "Application of an On-line Microwave Moisture Gauge at the Wet End." *Paper Trade Journal* (Sep. 11, 1972) pp. 54–57.

Joseph G. Dipre, "New England Closed Loop Control of Basis Weight." *Tappi*, vol. 46, No. 11 (Nov. 1963) pp. 178A–181A.

*Primary Examiner*—Constantine Hannaher
*Attorney, Agent, or Firm*—Davis Hoxie Faithfull & Hapgood

[57] ABSTRACT

A basis weight scanner using a beta-ray source and an electron detector on opposite sides of a web of wood pulp sheeting is used to calculate the weight of wood pulp advanced past a measuring location (e.g. into a cellulosic fibre production plant).

12 Claims, 3 Drawing Sheets

FLOW METER

BACKGROUND OF THE INVENTION

1. Field of the Invention

This invention relates to an improved method of and apparatus for determining the weight of web material fed to a processing station.

2. Description of Related Art

It is known, in a number of manufacturing processes, to use a basis weight scanner to monitor for variations in thickness of sheet material passing a monitoring point in a manufacturing process. One known form of basis weight scanner utilises a beta-particle emitter on one side of the moving sheet material and a beta-particle detector on the other side of the moving sheet material, the emitter and detector being moved together as a pair across a substantial part of the width of the sheet material to monitor variations in thickness of the sheet material by a sensing of real time variations in beta-particle absorption by the sheet material.

Such a basis weight scanner is used, for example, to monitor the output of a sheet extruder in a plastics processing plant downstream of an extruding head and, via a feedback loop, to adjust the performance of the extruding head to maintain substantially uniform product thickness across the width of the sheet material.

U.S. Pat. No. 4,854,730 discloses equipment for determining the content of fillers in paper which equipment uses a beta-ray source to evaluate the basis weight of the cellulose in the paper but the equipment described is not used to scan across the entire width of a web of paper to determine the total weight of cellulose as is practised by the present invention.

We have now found that a basis weight scanner can be used as a flow meter to determine the total weight of sheet material fed forward to a subsequent processing plant.

SUMMARY OF THE INVENTION

Accordingly, in its simplest form, the invention relates to the use of a basis weight scanner as a flow meter.

One particular application of the invention is in the monitoring of a pluri-layer web of cellulosic material (e.g. wood pulp) to determine, in real time, the total weight of cellulosic material passing the basis weight scanner and thereby, inter alia, to detect the loss of one layer of such material in the pluri-layer web.

In its apparatus aspect, the invention comprises means to advance a web, a scanning head adapted to sweep across the web in a direction transverse to its advance from side to side thereof, the scanning head generating a beam capable of being attenuated by the layers constituting the web and providing a beam-receiving means to determine, in real time, the degree of attenuation of the beam by the web, and computing means to determine from an aggregate of localised values of the attenuation determined in one scan of the scanning head across the web, the total weight of sheet material passing the measuring location in one scan of the scanning head.

Desirably the beam is a collimated beam of beta-rays generated from a radioactive source (e.g. Strontium 90) and the detector is an ionisation chamber sensitive to electrons passing through the web.

Suitably the scanning head also includes means to determine the moisture content of the web and such means can include a microwave source on one side of the web and a microwave detector on the other side of the web.

The transverse of the scanning head across the web is conventionally known as a scan. During each scan repeated determinations of the measured parameters at points spaced apart along the traverse are carried out. These point measurements are periodically grouped together and termed a slice. Computations are carried out at the end of each slice and at the end of each scan.

Desirably at the end of each slice the average basis weight (BW) for the slice is calculated as well as the measured length (ML) of web advanced during the slice. The web length advanced is suitably measured using a roller frictionally engaged with the pulp web surface. This roller can be coupled to a pulse generator thereby creating one pulse for each increment of length.

Desirably at the end of each scan the overall width (OW) of the scan and an average value for the basis weight (SA) of the web in that scan is calculated. The scan average basis weight is calculated from the average of all of the slice averages across the scan.

Any suitable computing means can be used to generate, at the end of each slice, the product of the computed scan average of basis weight (SA), the overall width of the scan (OW) (both of which could be determined on an earlier scan), and the measured length of the last slice (ML) and to present this product (SA×OW×ML) as a number of pulses whereby the actual weight of sheet material making up the web advanced in the last slice (DW) is available as a digital value.

Where a real time measure of moisture content is determined during each slice it is useful to determine a slice average of moisture content (M—expressed as weight percent) and to compute from the slice average of basis weight (BW) a slice average of dry basis weight (DBW) as the product of $$\frac{BW \times (100 - M)}{100}$$

and to use this DBW figure in place of BW to calculate the scan average of basis weight (SA) from which the number of pulses to represent the actual weight of sheet material advanced in the last slice can be calculated.

The invention has particular utility where the web comprises a plurality of layers of sheet material laid one on the other. In this case, to allow for the fact that the individual layers constituting the web may not be edge aligned, the scan width is made to exceed the width of each layer by an amount to ensure that each layer is fully scanned by the scanning head in its traverse over the web.

BRIEF DESCRIPTION OF THE DRAWINGS

The invention will now be described, by way of example, with reference to the accompanying drawings, in which.

DESCRIPTION OF THE PREFERRED EMBODIMENT

Figure 1:
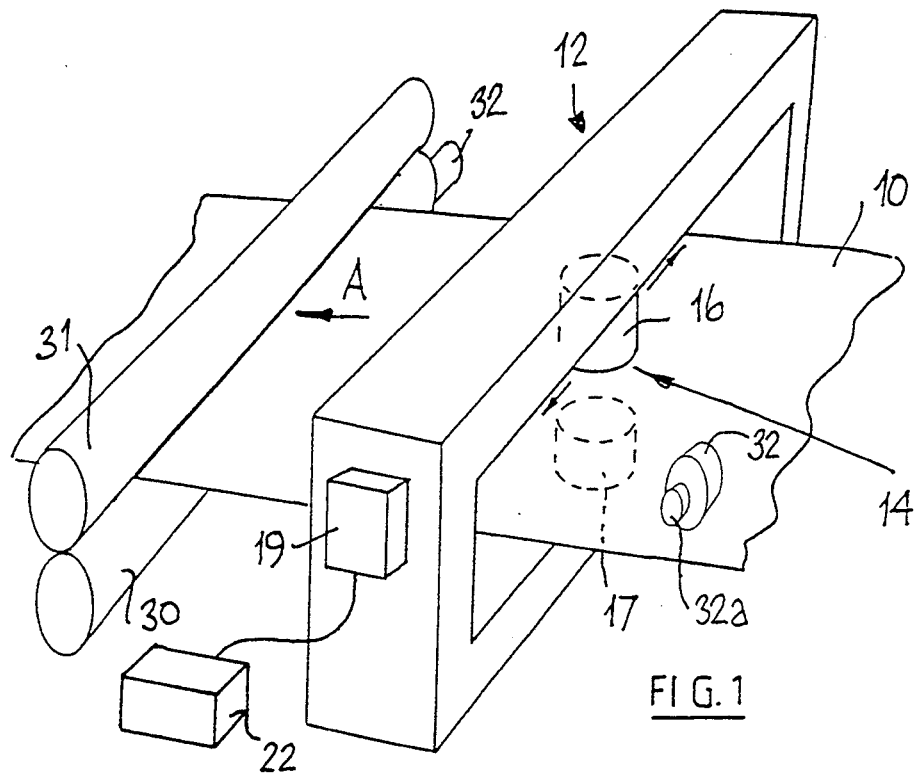
FIG. 1 is a schematic view of a web passing through a transversely mounted basis weight scanner.
Figure 2:
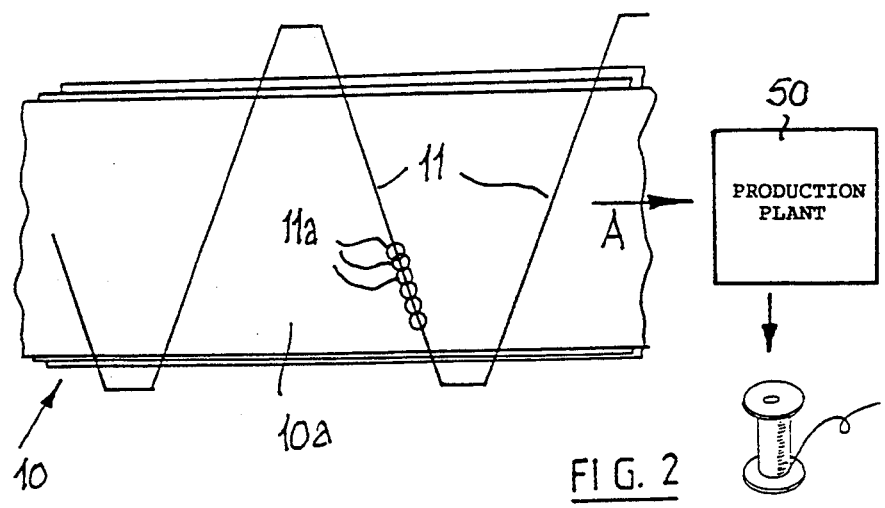
FIG. 2 is a plan from above of the arrangement in FIG. 1 showing the effective path of the scanning head of the scanner over the web in a plurality of traverses of the head.

FIG. 1 shows a web 10 advancing in the direction of an arrow A through a basis weight scanner unit 12 in which is movably located basis weight sensor equipment generally indicated by the arrow 14. The unit 12 can be a CIMLINE O-frame scanner available from Aeonic KGS of Newbury, Berkshire, United Kingdom, which movably supports the equipment 14 carrying it in accurately controlled scans from side-to-side across the web 10 at a pre-selected scan speed. The scanner unit 12 causes the equipment 14 to dwell briefly at the end of each traverse and accordingly, in plan, the scanning of the web would appear as shown in FIG. 2, each diagonal line 11 representing a uniform rate scan of the equipment 14 across the web 10.

The equipment 14 comprises a Strontium 90 source of beta-rays in an upper housing 16 and a Krypton electron sensor 17 located below the web 10. The source housing 16 and the sensor 17 are driven in precise synchronism from side-to-side across the web so that the sensor continuously receives those beta-particles emerging from the underside of the web. The basis weight sensor known as CIMLINE SR-90 (also available from Aeonic KGS) is particularly suitable for this application.

CIMLINE equipment has been widely used to control the output of a plastics extrusion head, it providing accurate measures of the basis weight (i.e. weight per unit area) of the extruded material across its width so that any irregularities can be corrected by making appropriate adjustments at the extrusion head. Although the equipment has been widely used for this purpose, so far as we are aware nobody has previously proposed it for a flow meter application to accurately determine the total weight of web material passing through the unit 12.

A particularly useful application of this invention relates to the determining of the total weight of wood pulp fed in a web to a cellulosic fibre processing plant 50 (see FIG. 2) and in particular to a web made up of a plurality of layers of sheets of wood pulp.

FIG. 2 shows the upper sheet 10a of such a pluri-layer web 10 and edge regions of some of the underlying sheets and it will be noted that each scan length of the equipment 14 exceeds the total width of all the sheets constituting the pluri-layer web 10.

Figure 4:
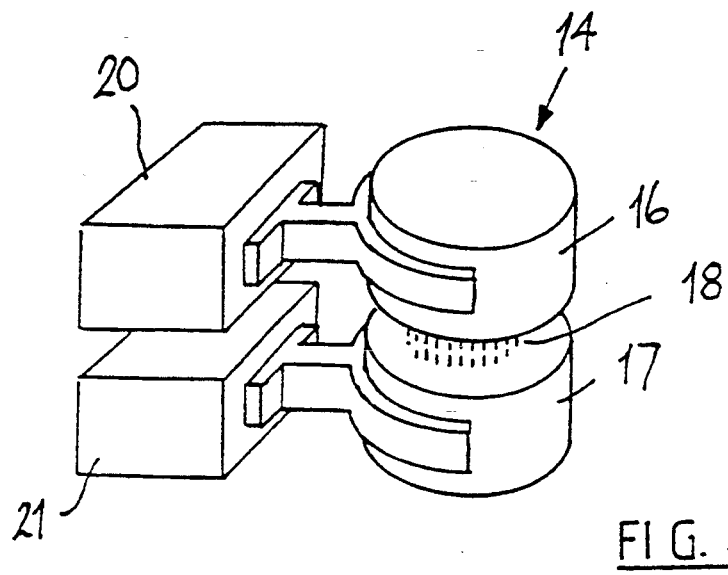
FIG. 4 is a schematic view of linked basis weight and moisture content sensors used in the arrangement of FIG. 1.

FIG. 4 illustrates, on the right thereof, the source housing 16 and the sensor 17 with the electron beam schematically illustrated at 18.

Figure 3:
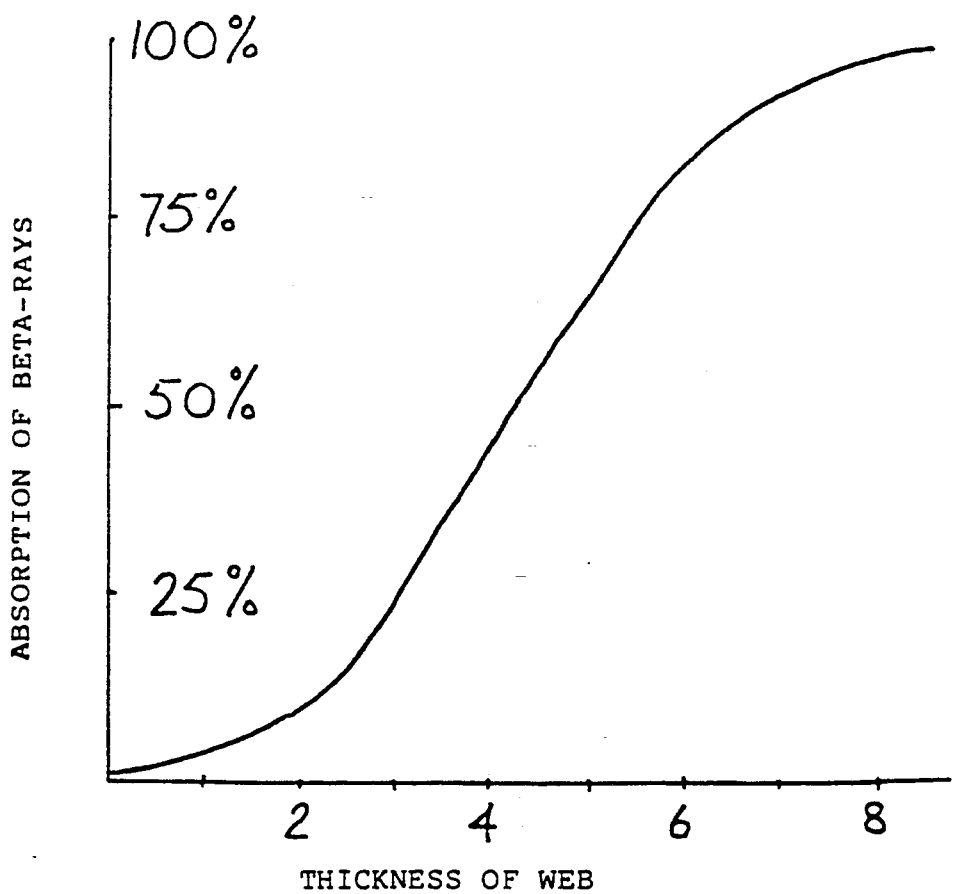
FIG. 3 is a graph showing the Absorption of beta-rays as a function of Thickness of Material in the path of the beam of beta-rays.

FIG. 3 shows the relationship between absorption of beta-rays (indicated between 0 and 100%) and the thickness of the web (in this case expressed as the number of layers in the web indicated between 1 and 8). From this graph it will be noted that the absorption is substantially linear over a central part of the curve (i.e. corresponding to between 3 and 6 sheets in the web) but for the seventh and eighth sheets the linear relationship is lost although even at this end of the absorption curve the absence of one sheet makes a significant difference in the absorption of the electron beam allowing for ready detection of the loss of one or more sheets from the web.

The graph shown in FIG. 3 represents the situation where sheets of bone-dry wood pulp are being used and is seriously distorted by the pressure of moisture in the sheets. Since, in practice, sheets of wood pulp can have varying moisture contents (typically between 3 and 10% by weight) any attempt to secure an accurate indication of the flow of bone-dry wood pulp past the scanning unit 12 must include accurate determinations of moisture content of the web and such determinations are undertaken by utilising a microwave source 20 and a microwave receiver 21 mounted, as shown in FIG. 4, respectively to the housing 16 and the sensor 17 of the beta-ray equipment 14.

The beta-ray equipment 14 is used, in the conventional manner, to derive numerical values (say $N_1$, $N_2$, $N_3$) for the level of absorption measured at a range of individual points spaced apart along one traverse of the web 10. Since the sensing commences before the web is between the source housing 16 and the sensor housing 17 and terminates after the entire width of the web 10 has been traversed, the earliest and latest absorption values derived in each traverse will represent zero basis weight. Between these low absorption readings will be a mass of individual point measurements. From these individual point measurements an overall average basis weight for the entire region traversed in the scan can be computed (e.g. in a computing means 19 shown in FIG. 1). The width of the scan is calculated from position sensors (not shown) on the drive mechanism of the equipment 14.

Figure 5:
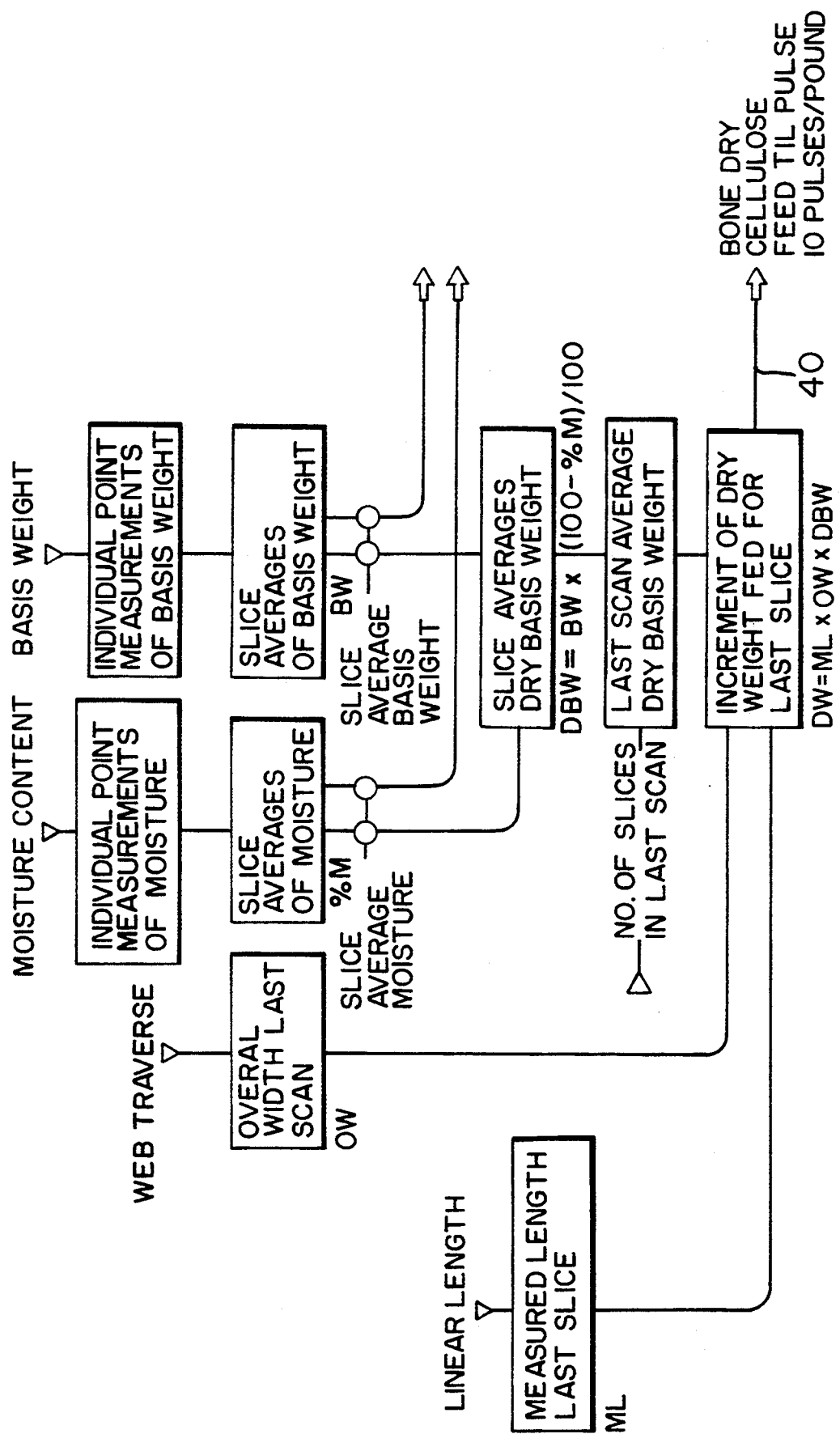
FIG. 5 is a simplified flow chart showing how a bone-dry feed rate for web material can be calculated.

FIG. 5 shows how the basis weight measurements and web width measurements can be combined with a measure of linear length of web pulled through the unit 12 by a nip pair 30, 31, and measured by a roller 32a which drives a pulse generator 32 to produce a pulse output (on line 40) which is indicative of the total dry weight of wood pulp fed forward. In one arrangement 22 pulses on line 40 represented precisely one kilogram of dry wood pulp so that if a specific recipe for a pulp-based feedstock required X kilograms, that precise weight of wood pulp would have been advanced through the unit 12 when 22X pulses had been received by a central pulse-counting unit (e.g. shown at 22 in FIG. 1).

FIG. 5 shows how moisture content can be computed at the same time as the basis weight measurements are being made, these moisture content measurements being made by means of the microwave source 20 and receiver 21 in a similar way to that used for the basis weight measurements.

Where moisture content does not vary greatly from batch to batch of web material passed through the unit 12 it may be unnecessary to monitor for moisture content but merely to allow a set figure (say 7.5% by weight) and to subtract the weight of the moisture from the measured weight of the wood pulp to provide the required dry weight figure.

From the foregoing it will be appreciated that the numerical figures determined during one complete scan of the web provide the basis for an accurate calculation of the total weight of cellulosic material advanced during the scan and also enable any irregularities in the web, which are large compared to the web advance during one scan, to be detected and allowed for. Thus where the web is a pluri-layer web of several separate sheets of wood pulp, the scanning method described can compensate for slightly different widths of sheet material making up the web, can take account of an imprecise alignment of the separate sheets one over the other to make the web and readily spot the disappearance of one sheet from the web (due, for example, to the expiry of one of a plurality of different rolls being used as sources for the sheets making up the web).

If one or more sheets is lost from the web, the scan average dry basis weight is corrected by multiplying the ratio of the number of sheets lost. This figure is used until a new scan average for a complete web with all its intended sheets is computed.

Although the equipment illustrated has been described with reference to the sensing of the weight of wood pulp flowing past the unit 12, it will be appreciated that the invention has applicability in other fields, the sole requirement being that the web material has an absorption of electrons which is a function of its basis weight.

What is claimed is:

1. Apparatus for determining the bone dry weight of wood pulp sheet material fed to a cellulosic processing plant past a measuring location which includes means to advance a pluri-layer web of the sheet material, a scanning head adapted to sweep across the entire width of the web in a direction transverse to its advance from side to side thereof, the scanning head including means to determine the moisture content of the web and generating a beam capable of being attenuated by the layers constituting the web and including a beam-receiving means to determine, in real time, the degree of attenuation of the beam of the web, and computing means to determine from an aggregate of localised values of the attenuation determined in one scan of the scanning head across the web the total weight of sheet material expressed in terms of bone dry wood pulp passing the measuring location in one scan of the scanning head.

2. Apparatus according to claim 1, wherein the beam is a collimated beam of beta-rays generated from a radioactive source and the beam-receiving means is an ionisation chamber sensitive to electrons passing through the web.

3. Apparatus according to claim 1, in which the moisture determining means includes a microwave source on one side of the web and a microwave detector on the other side of the web.

4. Apparatus according to claim 1, wherein means is provided to measure the length (ML) of web advanced past the measuring location in one scan of the scanning head.

5. Apparatus according to claim 4, wherein further means is provided
   a) for determining the basis weight (BW) of the web at a plurality of points along a sweep across the web,
   b) for determining the overall width (OW) of the scan across the web and
   c) for determining the scan average basis weight (SA) in one scan
   and wherein the computing means determines the product (SA×OW×ML) as a measure of the actual weight (DW) of sheet material passing the measuring location.

6. Apparatus according to claim 5, wherein means is provided to determine the average moisture content (M) of the sheet material and the computing means determines the dry basis weight (DBW) as the product of $$\frac{BW \times (100 - M)}{100}.$$

7. Apparatus according to claim 5, wherein the computing means is set to determine the absence of a layer of sheet material from the web by virtue of a reduction in the scan average basis weight (SA).

8. Apparatus according to claim 1, wherein the said beam is a collimated beam of beta-rays generated from a radioactive source and the beam-receiving means is an ionization chamber sensitive to beta-rays passing through the layers in the web and the moisture determining means includes a microwave source on one side of the web and a microwave detector on the other side of the web.

9. In a production plant for a cellulosic fibre from wood pulp sheets with apparatus to measure the weight of wood pulp fed as input to the plant, the improvement which comprises using a basis weight scanner as a flow meter for determining the weight of bone dry wood pulp sheeting fed to the plant.

10. A plant according to claim 9, wherein the wood pulp is fed to the plant as a pluri-layer web of sheets of wood pulp laid one on another, said web being fed through the basis weight scanner which includes a beta-ray source and a beam-receiving means to assess the weight of web material passing the source and moisture detecting means to determine the moisture content of the web and thereby compute the weight of bone dry sheeting fed to the plant, the basis weight scanner having a scan width which exceeds the width of the pluri-layer web and extends beyond both edges of the web.

11. Apparatus for determining the weight of bone dry cellulose in a pluri-layer web of wood pulp sheets advancing towards a processing plant past a measuring location, which, at said measuring location includes a scanning head adapted to sweep across the entire width of the pluri-layer web in a direction transverse to its advance from edge to edge thereof, the scanning head including means to determine the moisture content of the web and generating a beam capable of being attenuated by the layers of wood pulp constituting the web and providing a beam-receiving means to determine, in real time, the degree of attenuation of the beam by the layers in the web, and computing means to determine from an aggregate of localized values of the attenuation and moisture content determined in one scan of the scanning head across the web, the total weight of bone dry cellulose in the sheet material passing the measuring location into the plant.

12. Apparatus for determining the weight of bone dry cellulose in a pluri-layer web of wood pulp sheet material advanced past a measuring location to a cellulosic fibre processing plant, which at said measuring location includes a scanning head adapted to sweep across the web in a direction transverse to its advance from a position outwardly of one edge of the web to a position outwardly of the other edge thereof, the scanning head comprising (a) means for generating a beam of electrons capable of being attenuated by the layers of wood pulp constituting the web disposed on one side of the web and a beam-receiving means disposed on the other side of the web to determine, in real time, the degree of attenuation of the electron beam by the web, and (b) a microwave source disposed on one side of the web and a microwave detector disposed on the other side of the web to determine the moisture content of the web and computing means to determine from an aggregate of localized values of the attenuation and moisture content determined in one scan of the scanning head across the web, the total weight of bone dry cellulose passing the measuring location.

* * * * *